United States Patent
Baumann

(10) Patent No.: US 10,631,714 B2
(45) Date of Patent: Apr. 28, 2020

(54) SWING PRISM ENDOSCOPE

(75) Inventor: Harald Baumann, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 1067 days.

(21) Appl. No.: 13/045,321

(22) Filed: Mar. 10, 2011

(65) Prior Publication Data

US 2011/0257485 A1    Oct. 20, 2011

(30) Foreign Application Priority Data

Mar. 10, 2010    (DE) .................. 10 2010 010 948

(51) Int. Cl.
*A61B 1/00* (2006.01)
*G02B 23/24* (2006.01)
*A61B 1/055* (2006.01)

(52) U.S. Cl.
CPC ...... *A61B 1/00179* (2013.01); *A61B 1/00165* (2013.01); *A61B 1/00183* (2013.01); *G02B 23/2423* (2013.01); *A61B 1/055* (2013.01)

(58) Field of Classification Search
CPC .................................................. A61B 1/00183
USPC ................................ 600/173, 175; 359/431
See application file for complete search history.

(56) References Cited

U.S. PATENT DOCUMENTS

| | | | |
|---|---|---|---|
| 3,856,000 A | 12/1974 | Chikama | |
| 4,126,786 A | 11/1978 | Jones | |
| 4,556,292 A * | 12/1985 | Mathyssek et al. | 359/484.04 |
| 5,359,992 A * | 11/1994 | Hori et al. | 126/4 |
| 5,569,921 A | 10/1996 | Sato et al. | |
| 6,002,473 A * | 12/1999 | West | 356/153 |
| 6,560,013 B1 * | 5/2003 | Ramsbottom | 359/431 |
| 6,638,216 B1 * | 10/2003 | Durell | 600/173 |
| 7,523,848 B2 * | 4/2009 | Beatson et al. | 228/4.5 |
| 7,740,824 B2 * | 6/2010 | Godfried et al. | 423/446 |
| 2004/0127768 A1 * | 7/2004 | Huber et al. | 600/162 |
| 2006/0173242 A1 * | 8/2006 | Navok | A61B 1/0011 600/133 |
| 2009/0022951 A1 * | 1/2009 | Nelissen | B23K 26/0075 428/141 |
| 2010/0022838 A1 * | 1/2010 | Hoeg | 600/131 |

(Continued)

FOREIGN PATENT DOCUMENTS

| | | |
|---|---|---|
| DE | 2328595 A1 | 1/1974 |
| DE | 19927816 A1 | 1/2001 |

(Continued)

OTHER PUBLICATIONS

Bindig et al., Fibre-optic IR-spectroscopy for biomedical diagnostics, Spectroscopy 17 (2003) 323-344.*

(Continued)

*Primary Examiner* — Alexandra L Newton
*Assistant Examiner* — Rynae Boler
(74) *Attorney, Agent, or Firm* — Whitmyer IP Group LLC

(57) ABSTRACT

A swing prism endoscope with adjustable viewing direction includes a shaft with a proximal end and a distal end and a window of a transparent material that seals an opening on the distal end of the shaft so that it is fluid-tight. In addition the swing prism endoscope includes a pivotable prism on the distal end of the shaft for adjustable diversion of light that falls through the window into the shaft of the swing prism endoscope onto an object lens, where the pivotable prism is made of diamond.

17 Claims, 2 Drawing Sheets

(56) References Cited

U.S. PATENT DOCUMENTS

| | | | | |
|---|---|---|---|---|
| 2010/0030031 A1* | 2/2010 | Goldfarb | ............ | A61B 1/00066 |
| | | | | 600/163 |
| 2011/0123152 A1* | 5/2011 | Bicknell et al. | ................ | 385/36 |
| 2012/0029276 A1* | 2/2012 | Baumann | ........... | A61B 1/00064 |
| | | | | 600/101 |

FOREIGN PATENT DOCUMENTS

| | | | | | |
|---|---|---|---|---|---|
| WO | | 9966312 A1 | 12/1999 | | |
| WO | WO 2004046427 A1 | * | 6/2004 | ............. | C30B 25/02 |

OTHER PUBLICATIONS

European Search Report; Application No. 11 15 7263; dated Jun. 29, 2011; 9 pages.

* cited by examiner

SWING PRISM ENDOSCOPE

CROSS-REFERENCE TO RELATED APPLICATIONS

The present application claims priority of German patent application No. 10 2010 010 948.7 filed on Mar. 10, 2010.

FIELD OF THE INVENTION

The present invention relates to a swing prism endoscope with a viewing direction that can be adjusted by swinging a prism on the distal end of the endoscope and to a prism for a swing prism endoscope.

BACKGROUND OF THE INVENTION

Along with endoscopes for medical and non-medical technical applications, whose viewing direction is parallel to the longitudinal axis of the shaft of the endoscope, endoscopes with other fixed viewing directions were developed from an early time. The viewing direction of an endoscope is always understood here and in the following text to mean the direction, looking from the distal end of the endoscope, in which an object is situated that appears in the center of the image captured by the endoscope. However, with many applications a fixed viewing direction is a disadvantage. In the worst case, the endoscope must be repeatedly replaced, for example during a medical procedure. In such cases it is advantageous to use an endoscope with a viewing direction that can be adjusted or displaced in situ.

A swing prism endoscope comprises on the distal end a pivotable prism, on whose border surfaces light impinging into the endoscope is broken up and reflected before being conveyed to the proximal end of the endoscope, for example by means of a rod lens system. The viewing direction can be adjusted by swinging the prism around an axis perpendicular to the longitudinal axis of the endoscope shaft.

Conventional swing prism endoscopes, however, have an unsatisfactory viewing direction range. If the viewing direction range is intended to include a viewing direction parallel to the axis of the endoscope shaft (zero degrees), for some time now only a small viewing direction range could be achieved, with less than 45 degrees between its extreme viewing directions. A large viewing direction range, with 75 degrees or more between its extreme viewing directions, for some time has included at best, for example, viewing directions of 45 to 120 degrees or 15 to 120 degrees or 10 to 115 degrees to the axis of the endoscope shaft.

SUMMARY OF THE INVENTION

An object of the present invention consists in providing an improved swing prism endoscope, in particular a swing prism endoscope with a greater viewing direction range, and an improved prism for a swing prism endoscope, in particular a prism that makes possible a greater viewing direction range in a small spatial area whose extent, for example, is restricted by compatibility with conventional trocars and their standardized lumina.

This object is achieved through the content of the independent claims.

Refinements are indicated in the dependent claims.

Embodiments of the present invention are based on the idea of constructing the pivotable prism of a swing prism endoscope of diamond. Diamond for some time has been used in optics only where its superior mechanical, chemical and thermal properties were required or were advantageous. The extreme hardness, great heat-conductivity and high resistance to many chemicals are used in thin, optically transparent windows that separate a fluid from a vacuum or from another fluid, and in coatings. For a long time now, diamond has not been considered as a material for optical elements such as lenses or prisms. Reasons for this may have been the high manufacturing costs, strong restrictions in achievable geometric parameters and—particularly observed in polycrystalline diamond or the kind that includes numerous faulty spots—double refraction.

The present invention is based on the recognition that the pivotable prism of a swing prism endoscope, contrary to optical elements for many other applications, comprises a comparatively small volume. It is therefore possible to produce the prism from diamond, and in particular to do so at reasonable cost.

One advantage of a pivotable prism for a swing prism endoscope made of diamond consists in the fact that the prism can be produced with especially compact dimensions. Another advantage is the fact that diamond, in particular monocrystalline diamond, has a high transparency to light in the wavelength range visible to the human eye. In addition, diamond has a relatively high refractive index and a low dispersion for visible light. When monocrystalline diamond is produced by means of chemical vapor deposition (CVD), a very low refringence can be achieved.

Altogether, using diamond for a pivotable prism of a swing prism endoscope makes possible a viewing direction range that includes viewing directions from zero degrees (parallel to the longitudinal axis of the endoscope shaft) to far above 90 degrees, in particular up to 115 degrees or 120 degrees. Such a great viewing direction range has not been achieved in any other swing prism endoscope for a long time. As mentioned above, the viewing direction is the direction from the distal end of the endoscope to those sites that appear in the center of the image in viewing through the endoscope, independently of whether this image is observed directly through an eyepiece on the proximal end of the endoscope or is captured by means of a video camera.

A swing prism endoscope with adjustable viewing direction includes a shaft with a proximal end and a distal end, a window (in particular a curved window) of a transparent material that seals an opening on the distal end so that it is fluid-tight, and a pivotable prism on the distal end of the shaft for adjustable diversion of light falling through the window into the shaft of the swing prism endoscope onto an object lens, where the pivotable prism is made of diamond. The pivotable prism is in particular constructed of monocrystalline diamond, which for example is generated by chemical vapor deposition.

In a swing prism endoscope as described here, it is also possible to provide antireflective coatings on a light entry surface and on a light exit surface of the pivotable prism.

A swing prism endoscope as described here can include a viewing direction range within which the viewing direction of the swing prism endoscope can be adjusted and which includes an axial direction and a direction perpendicular to it. The axial direction is the direction of the longitudinal axis of the shaft of the swing prism endoscope.

A swing prism endoscope as described here can include a viewing direction range with an angle of at least 110 degrees, in particular of at least 120 degrees, between extreme viewing directions. This viewing direction range can include a viewing direction parallel to the longitudinal axis of the endoscope.

A prism for a swing prism endoscope includes a light entry surface, a reflecting base surface, and a light exit surface, where the prism is constructed of diamond, in particular of monocrystalline diamond. The prism can be generated by chemical vapor deposition. In addition the prism can comprise antireflective coatings on the light entry surface and on the light exit surface.

BRIEF DESCRIPTION OF THE DRAWINGS

Hereinafter, embodiments are described in greater detail with reference to the appended drawings, which are as follows.

DETAILED DESCRIPTION OF THE INVENTION

Figure 1:
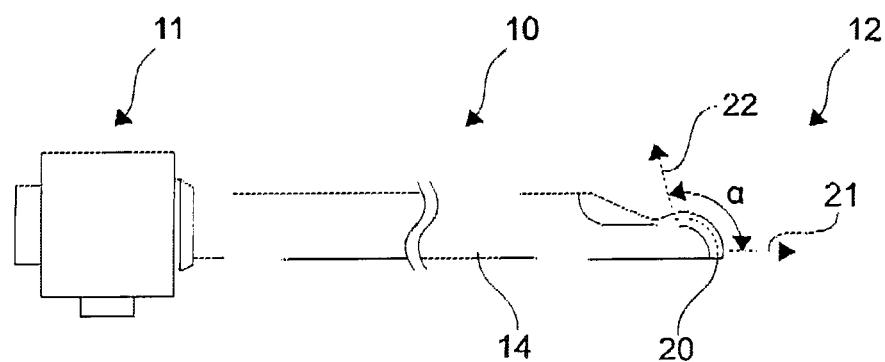
FIG. 1 shows a schematic depiction of a swing prism endoscope.

FIG. 1 shows a schematic depiction of an endoscope 10 with a proximal end 11 and a distal end 12. The proximal end 11 of the endoscope 10 is not treated in detail hereinafter. It can include an eyepiece, a coupling to a light conductor cable for coupling light from a light source to illuminate an object that is to be observed by the endoscope, a video camera, a coupling to a light conductor cable to transmit an image by means of an arranged bundle of lightwave conductors and/or other elements that are not depicted in FIG. 1 or are only referred to.

A shaft 14 extends from the proximal end 11 to the distal end 12 of the endoscope 10. Reference numbers 11, 12 are used hereinafter to indicate also the proximal end or the distal end of the endoscope 10. The shaft 14 comprises, for example, a constant circular-shaped cross-section. At the distal end 12, the shape of the shaft 14 diverges from cylindrical shape so that the cross-section of the shaft also on the distal end 12 does not extend beyond the contour provided by the prevailingly cylindrical shape of the shaft 14. The shaft 14 is, in particular, rigid and comprises a rod lens system to transmit an image from the distal end 12 to the proximal end 11 of the endoscope 10. Alternatively the shaft 14 can be flexible. In this case the shaft 14 contains, for example, an arranged bundle of lightwave conductors to transmit an image from the distal end 12 to the proximal end 11 of the endoscope 10, or a video camera is positioned close to the distal end 12 in the shaft 14 of the endoscope 10.

A curved window 20 of a transparent material is provided on the distal end 12 of the endoscope 10. The window 20 seals an opening on the distal end 12 of the endoscope 10 so that it is fluid-tight, in particular hermetically insulated. The window 20 comprises, for example, the geometric shape of a portion of a cylindrical sleeve, so that the axis of the cylinder is perpendicular to the plane of projection of FIG. 1. Positioned close to the window 20 in the endoscope 10 is a prism that is described hereinafter in greater detail with reference to FIGS. 2 through 4. The movable prism and the curved window 20 make it possible to select any desired viewing direction within a viewing direction range. As mentioned, the viewing direction is the direction looking from the distal end 12 of the endoscope 10 in which an object or a site is situated that is located in the center of the image acquired by the endoscope 10 during observation by means of an endoscope 10. Indicated in FIG. 1 are two extreme viewing directions 21, 22 that form an angle alpha. One or more light exit surfaces can be positioned beside the window and through said surfaces light can emerge for illuminating an object that is to be observed by means of the endoscope 10.

Figure 2:
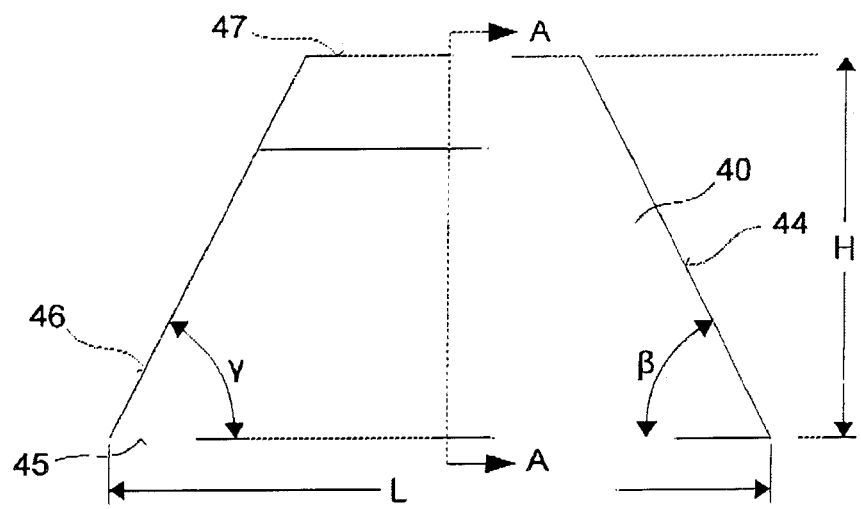
FIG. 2 shows a schematic depiction of a prism for a swing prism endoscope.
Figure 3:
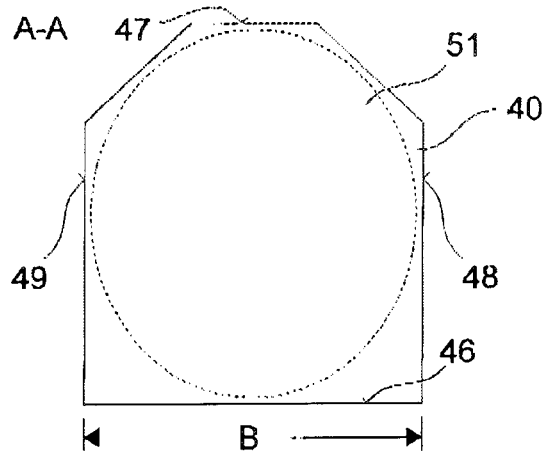
FIG. 3 shows a schematic depiction of a section through the prism of FIG. 2.

FIGS. 2 and 3 show schematic depictions of the aforementioned prism 40 made of diamond in the endoscope 10 close to the distal end 12 of the endoscope 10. The plane of projection of FIG. 2 is parallel to the plane of projection of FIG. 1. FIG. 3 shows a section through the prism 40 along the plane A-A indicated in FIG. 2. The ability of the prism 40 to pivot and its optical effect are explained hereinafter with reference to FIGS. 4 and 5.

The prism 40 comprises a light entry surface 44, a reflecting base surface 45 and a light exit surface 46, each of which is perpendicular to the plane of projection of FIG. 2. The light entry surface 44 and light exit surface 46 each comprise an antireflective coating. The reflecting base surface 45 is mirrored for a high degree of reflectivity. A roof surface 47 opposite the reflecting base surface 45 has no optical function. The light entry surface 44 and the light exit surface 46 can meet in an edge that is perpendicular to the plane of projection of FIG. 2. This would cause an increased space requirement for prism 40 in the endoscope 10, however.

Lateral surfaces 48, 49 are parallel to the plane of projection of FIG. 2 and perpendicular to the plane of projection of FIG. 3. It can be recognized in FIG. 3 that the edges between the roof surface 47 and the lateral surfaces 48, 49 can comprise broad fibers.

FIG. 3 in addition shows in broken lines the projection 51 of the edges of the approximately elliptical area of the light exit surface 46 through which light passes that contributes to generating an image by the endoscope 10. The distance L between the edges in which the light entry surface 44 and/or the light exit surface 46 border on the reflecting base surface 45 is 5 mm to 7 mm. The distance H between the reflecting base surface 45 and the roof surface 47 of the prism 40 is 2.5 mm to 3.5 mm. The distance B between the lateral surfaces 48, 49 is 2 mm to 3 mm. The angle beta between the light entry surface 44 and the reflecting base surface 45 and the angle gamma between the reflecting base surface 45 and the light exit surface 46 are each between 50 degrees and 70 degrees, in particular between 55 degrees and 65 degrees. The angles beta, gamma can be identical or different from one another.

Figure 4:
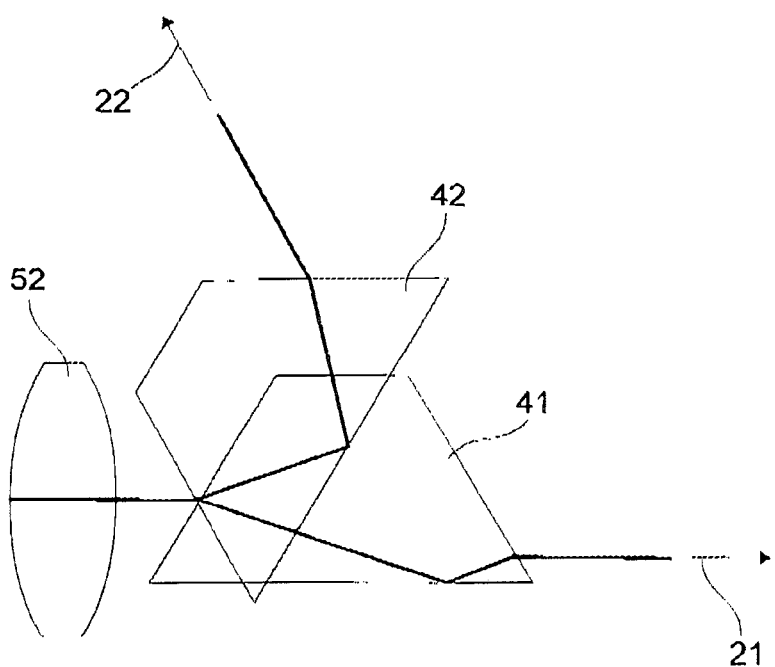
FIG. 4 shows a schematic depiction of a swing prism in two different positions on the distal end of an endoscope.

FIG. 4 shows the prism 40 of diamond as described above with reference to FIGS. 2 and 3, in two extreme positions 41, 42 between which the prism 40 can be adjusted freely. The plane of projection of FIG. 4 is parallel to the planes of projection of FIGS. 1 and 2. In addition, FIG. 4 shows an object lens 52 or a lens for capturing and retransmitting light that falls through the window 20 discussed above with reference to FIG. 1 into the endoscope 10 and is diverted by the prism 40.

For each of the two extreme positions 41, 42 of the prism 40, one beam is shown, which emanates from an object that is situated in the viewing direction 21, 22 and that therefore appears in the center of an image acquired by means of the endoscope 10. The angle between the two extreme viewing directions 21, 22 in this example is of approximately 120 degrees, with the first extreme viewing direction 21 parallel to the axis of the shaft 14 of the endoscope 10.

Figure 5:
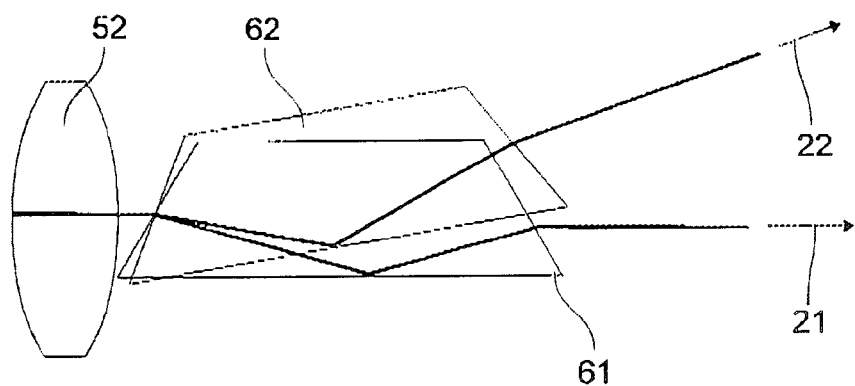
FIG. 5 shows a schematic depiction of a swing prism in two different positions on the distal end of a conventional endoscope.

FIG. 5 corresponds to FIG. 4, but with a prism being shown in two extreme positions 61, 62, said prism being made not from monocrystalline diamond produced by chemical vapor deposition but rather from a glass. Here one of the two extreme positions permits a viewing direction in the axial direction.

The two extreme positions 61, 62 are fixed by the spatial area that is available to the prism at the distal end 12 within the endoscope 10. It can be recognized that the prism is clearly longer than the inventive prism of diamond presented above with reference to FIG. 4 and therefore can be rotated only over a clearly lesser angle. Subsequently, also the angle between the two extreme viewing directions 21, 22 is clearly smaller.

What is claimed is:

1. A prism for a swing prism endoscope, the prism comprising: a light entry surface, a reflecting base surface, and a light exit surface; the prism is made of monocrystalline diamond, the prism having antireflective coatings on the light entry surface and on the light exit surface; a viewing direction ranges from a first position to a second position that is 120 degrees from the first position; a distance L between edges in which the light entry surface and the light exit surface border on the reflecting base surface is between 5 mm and 7 mm.

2. The prism of claim 1, further comprising a roof surface.

3. The prism of claim 2, wherein a distance H between the reflecting base surface and the roof surface of the prism is between 2.5 mm to 3.5 mm.

4. The prism of claim 1, wherein a distance B between lateral surfaces is 2 mm to 3 mm.

5. The prism of claim 1, wherein an angle beta between the light entry surface and the reflecting base surface is between 50 degrees and 70 degrees.

6. The prism of claim 1, wherein an angle gamma between the reflecting base surface and the light exit surface is between 50 degrees and 70 degrees.

7. The prism of claim 2, wherein the roof surface has no optical function.

8. The prism of claim 1, wherein the prism is made by chemical vapor deposition.

9. The prism of claim 1, wherein the diamond has a high refractive index.

10. The prism of claim 1 wherein the light entry surface and the light exit surface meet in an edge that is perpendicular to a plan of projection.

11. A swing prism endoscope with adjustable viewing direction, comprising: a shaft with a proximal end and a distal end; a window of a transparent material that seals an opening on the distal end of the shaft so that it is fluid-tight; and a pivotable prism made of monocrystalline diamond, the prism having antireflective coatings on a light entry surface and on a light exit surface of the prism, the pivotable prism located on the distal end of the shaft for adjustable diversion of light falling through the window into the shaft of the swing prism endoscope onto an object lens, wherein the monocrystalline diamond is produced by means of chemical vapor deposition (CVD), wherein no cross-section of the shaft on the distal end extends beyond a contour provided by a prevailingly cylindrical shape of the shaft, wherein a distance L between edges where the light entry surface and the light exit surface border on a reflecting base surface is approximately 5 mm to 7 mm, wherein a distance H between the reflecting base surface and a roof surface of the prism is approximately 2.5 mm to 3.5 mm, and wherein a distance B between lateral surfaces of the prism is approximately 2 mm to 3 mm.

12. The swing prism endoscope of claim 11, wherein the shaft is fluid-tight.

13. The swing prism endoscope of claim 11, further comprising a rod lens system to transmit an image from the distal end to the proximal end of the endoscope.

14. The swing prism endoscope of claim 11, wherein the light entry surface and the light exit surface of the prism are perpendicular to a viewing direction.

15. The swing prism endoscope of claim 11, wherein the window is curved.

16. The swing prism endoscope of claim 11, wherein viewing angle is at least 120 degrees.

17. The swing prism endoscope of claim 11, wherein the endoscope is hermetically insulated.

* * * * *